United States Patent [19]
Rönnberg

[11] Patent Number: 5,897,544
[45] Date of Patent: Apr. 27, 1999

[54] ABSORBENT ARTICLE

[75] Inventor: Peter Rönnberg, Mölndal, Sweden

[73] Assignee: SCA Mölnlycke AB, Göteborg, Sweden

[21] Appl. No.: 08/793,560

[22] PCT Filed: Sep. 15, 1995

[86] PCT No.: PCT/SE95/01049

§ 371 Date: Feb. 27, 1997

§ 102(e) Date: Feb. 27, 1997

[87] PCT Pub. No.: WO96/08225

PCT Pub. Date: Mar. 21, 1996

[30] Foreign Application Priority Data

Sep. 16, 1994 [SE] Sweden .................................. 9403110

[51] Int. Cl.⁶ ................................................ A61F 13/15
[52] U.S. Cl. .................................. 604/385.2; 604/385.1; 604/378
[58] Field of Search ............................ 604/385.1, 385.2, 604/382, 378

[56] References Cited

U.S. PATENT DOCUMENTS 2,538,758  1/1951 Bricmont ............................ 604/385.2
4,413,996  11/1983 Taylor ..................................... 604/382

FOREIGN PATENT DOCUMENTS

| 0 140 471 A1 | 5/1985 | European Pat. Off. . |
| 0 357 298 A2 | 3/1990 | European Pat. Off. . |
| 0 359 410 A1 | 3/1990 | European Pat. Off. . |
| 2 159 693 | 12/1985 | United Kingdom . |
| 2 159 693A | 12/1985 | United Kingdom . |
| WO 94/14395 | 7/1994 | WIPO . |

Primary Examiner—Robert A. Clarke
Attorney, Agent, or Firm—Burns, Doane, Swecker & Mathis, L.L.P.

[57] ABSTRACT

The invention relates to an absorbent article, such as diaper, an incontinence protector or the like. In order to prevent urine from being mixed with faeces in the rear area of the article, an essentially liquid impermeable membrane is laid between an inner cover layer and an absorbent layer laying outside of it. The article has an opening to a pocket lying outside the membrane to make possible transport of urine from a front wetting area of the article to a rear area of the absorbent body which lies outside the membrane.

20 Claims, 3 Drawing Sheets

ABSORBENT ARTICLE

The present invention claims priority to International Application PCT/SE95/01049 filed Sep. 15, 1995.

TECHNICAL FIELD OF THE INVENTION

The present invention relates to an absorbent article such as a diaper, an incontinence protector or the like, comprising an absorbent body with at least one elongated absorbent layer, which, on its inside facing the user is covered with a liquid permeable inner cover layer and which on its outside facing away from the user is covered by a liquid impermeable outer layer, said inner and outer cover layers being joined to each other along a peripheral edge of the absorbent body, said article having a rear, faeces receiving area and a front, urine absorbing wetting area.

BACKGROUND OF THE INVENTION

When wearing absorbent articles, such as diapers and incontinence protectors, it is important to prevent, as much as possible, urine from spreading backwards in the article so as to come into contact with the anus and the skin surrounding it. It is even more important to prevent urine from being mixed with faeces in the rear portion of the article and then coming into contact with the sensitive area around the anus.

AU-B-45 217/85 describes a diaper with a collection pouch for collecting urine and keeping the urine separate from the body of the wearer. The diaper comprises an inner layer of hydrophobic, essentially liquid impermeable material. This layer is provided with an oblong opening at the front portion of the crotch area. On either side of the opening, elastic elements are mounted which, during use, keep the inner layer against the body of the user. An absorbent body is bent laterally under the influence of the elastic elements and is spaced from the inner layer. Thus, a channel is formed for collecting urine and faeces, which are thereafter spread over the absorbent body beneath the liquid impermeable inner layer and are kept separate from the skin.

GB-A-2 159 693 discloses a diaper which is provided with collecting pockets at the end edges or at least at one end edge, for example the rear portion. The collecting pocket is formed by layers of liquid permeable material covering a portion of the diaper and being fixed thereto along a waist edge and a portion of the lateral edges. On the layer edge facing the crotch area, i.e. along the opening of the pocket, there is applied an elastic element transversely, which strives to pull the layer together laterally and create a small gap between the layer and an absorbent body. These collecting pockets are intended to prevent leakage of primarily faeces.

Furthermore, EP-A-0 357 298 and EP-A-0 359 410 describe absorbent articles where solid excrements are removed from the skin of the user with the aid of collecting pockets. The inner layer of the article is liquid permeable and has a small opening, through which solid excrement is conducted to an absorbent body. The intention is in this case that the opening should be small and correctly placed. An arrangement of elastic means can be disposed on the inner layer in order to adjust the position of the opening and thus minimize its size.

None of these previously known absorbent articles is, however, constructed to effectively prevent urine, especially in a rapid heavy emission by a wearer lying on his back, from reaching the faeces receiving area of the article and thus coming into contact with the area surrounding the anus of the wearer. This problem is particularly pertinent to incontinence protectors which are to be worn for a relatively long period, for example over a night, by a patient lying in bed.

SUMMARY OF THE INVENTION

In order to solve this problem, the article of the type described by way of introduction is characterized in its broadest aspect in that in the rear faeces receiving area of the article, there is inlaid an essentially liquid impermeable membrane between the inner cover layer and the elongated absorbent layer, thereby enabling transport of urine from the front wetting area of the article to the rear, outside the membrane lying area of the absorbent body without permitting urine from being mixed with faeces in the rear area and there coming into contact with the skin of the wearer.

According to a simple embodiment of the absorbent article according to the present invention, the inner cover layer, at least in the faeces receiving area of the article, has a liquid absorbing structure, for example a high bulk material of hydrophilic character, and lying directly inside the liquid impermeable membrane.

According to a suitable embodiment, the absorbent body has, firstly, an outer absorbent layer, extending over essentially the entire length of the article, and secondly, at least one inner absorbent layer extending over the faeces receiving area of the article, between the essentially liquid impermeable membrane and the inner cover layer. The absorbent body can, of course, comprise a plurality of absorbent layers, but at least the layer lying closest to the skin of the user, i.e. the inner layer, should be inaccessible to urine in the faeces receiving area by means of the essentially liquid impermeable membrane.

In order to make possible rapid spreading and absorption of urine over the entire longitudinal absorbent body in event of rapid and heavy emission of urine over the wet area, it is further suggested that means be disposed to, at a position between the front and back areas of the article, to facilitate transport of urine from the front wetting area of the article to a rear area of the absorbent body. Suitably, such means or aid according to the invention can consist of a pocket extending in an area between the membrane and the elongated absorbent layer, whereby the heavy urine flow can also be rapidly transported to the rear absorbent layer portion lying under the membrane, both through the same as well as above the same via the pocket and thereby be absorbed in the absorbent layer without urine being allowed to be mixed with any faeces in the rear portion of the article.

Such an aid can also comprise a layer of material rapidly permeable to liquid, placed at least partially between the membrane and the elongated absorbent layer in order to rapidly conduct urine into the pocket in the rear portion of the article. This material can consist of a batting material or the like.

The absorbent body can comprise a plurality of inner absorbent layers, located in the faeces receiving area of the article, at least the absorbent lying closest to the inner cover layer being insulated from underlying absorbent layers by means of the substantially liquid impermeable membrane. The urine absorbing capacity of the article is thereby increased.

The front area of the liquid impermeable membrane is suitably directed against a front portion of the rear faeces receiving area of the inner cover layer and is joined thereto in order to form at the opening to the pocket a front edge protection of the inner absorption layer, so that urine cannot penetrate therein. The rear portion of the inner cover layer covering the wetting area is fixed to the liquid impermeable membrane at least at the side portions of the product, for example behind the connection of the membrane to the front portion of the rear, faeces receiving area of the inner cover layer, so that a transverse opening through the pocket can be formed between the front portion of the liquid impermeable membrane and the elongated absorbent layer lying outside.

In order to further prevent urine from the wetting area from flowing over into the rear faeces receiving area of the article, especially during heavy urine emissions when the wearer is lying down, there is arranged on the inside of the article an erected barrier means which can be formed of the front portion of the faeces receiving area of the inner cover layer or of the front portion of the liquid impermeable membrane. This barrier means can have a hose-shaped fold in which an elastic element is mounted contributing to keeping the barrier means erect.

Furthermore, it is suitable to arrange means for moving apart the membrane and the opposite portion of the elongated absorbent layer to form the pocket with the associated opening. These means can consist of transverse elastic elements mounted in the rear faeces receiving area of the inner cover layer and/or transverse elastic element mounted in the liquid impermeable membrane.

The barrier means can further comprise portions extending completely or partially around the wetting area of the article.

BRIEF DESCRIPTION OF THE FIGURES

The invention will be described in more detail below with reference to the accompanying drawings, in which.

DETAILED DESCRIPTION OF THE INVENTION

Figure 1:
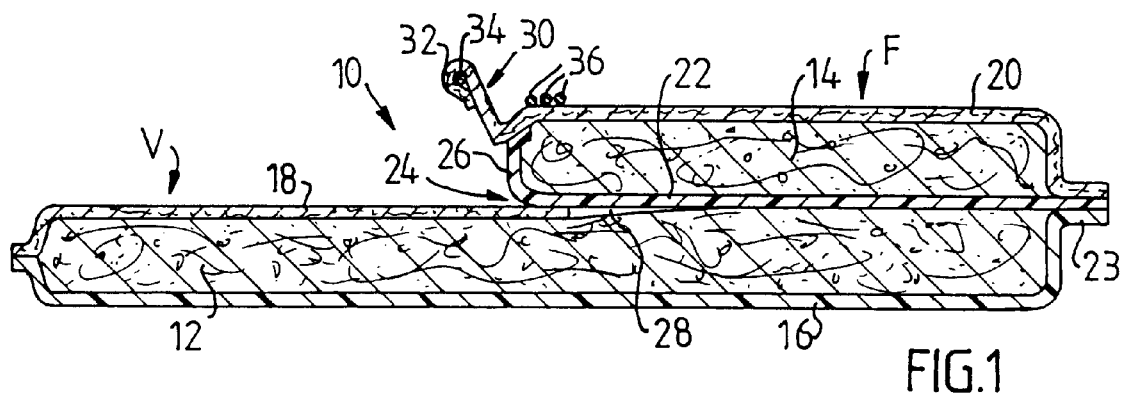
FIG. 1 is a schematic longitudinal sectional view of one embodiment of an absorbent incontinence protector according to the present invention.

FIG. 1 shows schematically the principal construction of an embodiment of an absorbent article 10, namely an incontinence protector or a diaper, called below the diaper. The diaper 10 has an absorbent body, which comprises an elongated absorbent layer 12 extending over the entire length of the diaper 10, and a shorter inner absorbent layer 14 which is located only over a rear faeces receiving area of the diaper 10. The absorbent layers 12 and 14 can consist of suitable absorbent materia which is known per se, for example fibres of fluff pulp or other absorbent fibres. Even so-called super-absorbents, i.e. substances with an absorption capacity many times exceeding the weight of the substances themselves, can be included in the absorbent layers 12, 14. The absorbent layer 12 is, on its side intended to face away from the user, covered with a liquid impermeable outer cover layer 16, which can consist of polyethylene, for example. On its side facing the user, the diaper 10 has a liquid permeable inner cover layer, which comprises a front portion 18 covering a front urine absorbing wetting area V of the elongated absorbent layer 12, and a rear portion 20 covering a rear faeces receiving area F of the diaper 10, namely the inner absorbent layer 14. The inner cover layer 18, 20 can consist of a flexible non-woven fibre fabric.

Between the rear portion of the elongated absorbent layer 12 and the inner absorbent layer 14, there is laid an essentially liquid impermeable membrane 22, which has the purpose of preventing urine from being conducted into the inner absorbent layer 14. The membrane 22 can consist of an entirely liquid impermeable plastic film or of a hydrophobisized fibre fabric material, which can "breathe" but which is essentially liquid impermeable. "Essentially liquid impermeable" refers in this context to both completely liquid impermeable and substantially liquid impermeable. The inner and outer cover layers 16 and 18, 20, respectively, and the membrane 22 are fixed to each other along the peripheral edge 23 of the diaper 10. The front portion 26 of the membrane 22 is folded up over the front edge of the absorbent layer 14 and is fixed to the front portion of the rear, faeces receiving portion 20 of the inner cover layer. The rear portion of the cover layer 18 covering the wetting area is fixed to the membrane 22 at least at the lateral edge portions 23 of the article.

Figure 2:
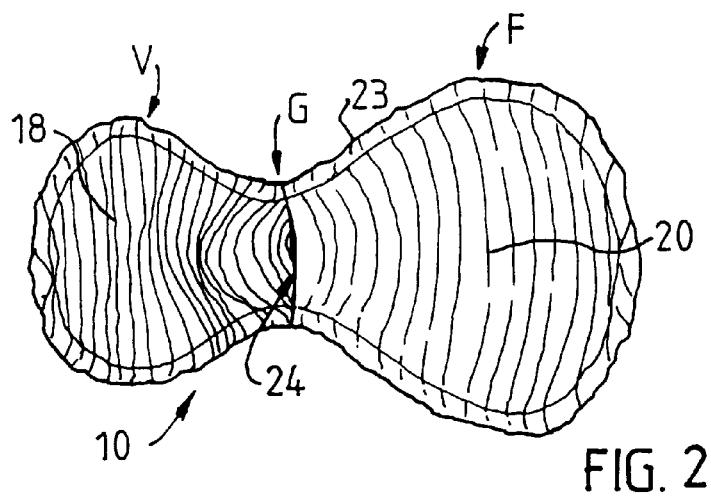
FIG. 2 is a view from above of the protector in FIG. 1.

As can be seen in FIG. 2, the diaper 10 has an hour-glass shape, where the rear, faeces receiving area F has a greater area than the front wetting area V, a narrow crotch area G joining the areas F and V. The configuration of the diaper can be varied in many different ways within the scope of the invention.

Figure 3:
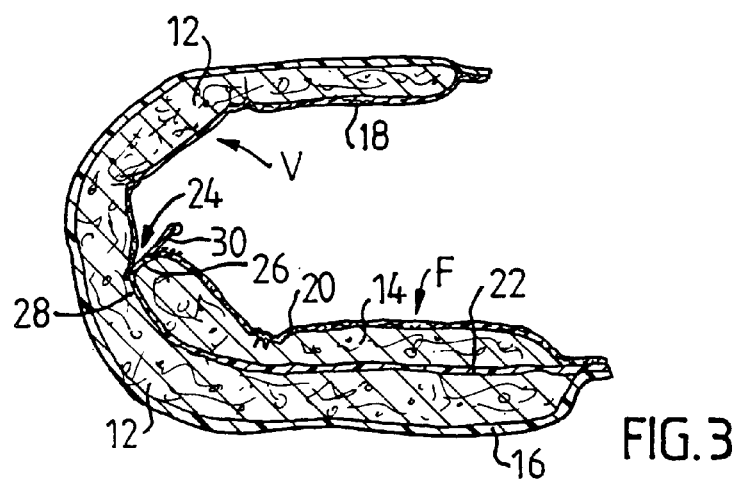
FIG. 3 shows the incontinence protector in FIGS. 1 and 2 in a use position on a patient lying on his back.

As can be seen in more detail in FIG. 3, which shows a diaper in the use state, the diaper 10 is made in the area between the wetting area V and the faeces receiving area F, suitably the crotch area G, so that a transverse slot or opening 24 can be formed between the front end portion 26 of the essentially liquid impermeable membrane 22 and a portion of the elongated absorbent layer 12 lying outside said membrane. This opening 24 is designed to conduct urine into a pocket 28 formed behind the opening 24 between the outside of the membrane 22 and at least a portion of the opposing portion of the absorbent layer 12, where the urine can be distributed over and absorbed in the rear portion of the absorbent layer 12. This is particularly the case when the wearer of the article is lying down and/or when the emission of urine by the wearer is so great that the front wetting area of the absorbent layer 12 does not have time to absorb all the urine and spread it backwards in the layer 12. Some of the urine will run along the outside of the inner cover layer 18 and via the opening 24 and the pocket 28 down into the rear portion of the absorbent layer 12. Thus sudden heavy urine emissions can be rapidly distributed and absorbed by the elongated absorbent layer 12 at the same time as the urine therein is prevented by the membrane 22 from penetrating into the inner absorbent layer 14 and there, with or without being mixed with faeces, coming into contact with the skin around the anus.

Figure 4:
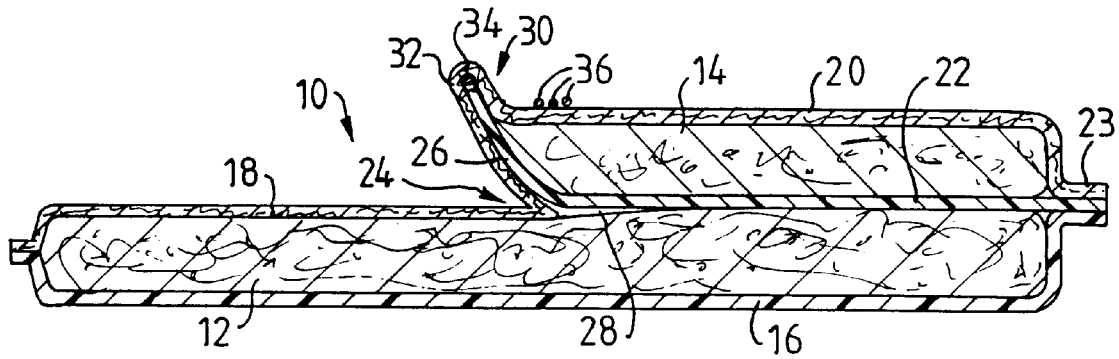
FIG. 4 shows an embodiment similar to FIG. 1 but with an unbroken inner cover layer.
Figure 6:
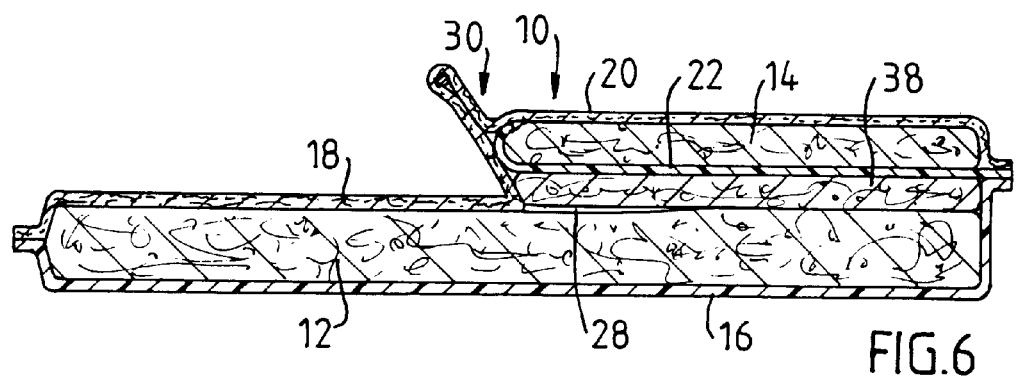
FIG. 6 shows another embodiment of an absorbent incontinence protector according to the present invention in longitudinal section.

In the embodiment according to FIGS. 1–3, the inner cover layer 18, 20 is divided and shows a break in the area between the front and the rear areas V and F of the diaper 10. The opening 24 to the pocket 28 can thus be left completely free to facilitate rapid flowing of urine into the pocket. However, it is also possible to make the inner cover layer without breaks, as is shown in FIGS. 4 and 6, for example. The inner cover forms thereby a fold in the area of the opening into the pocket. By virtue of the fact that the inner cover layer in itself has great liquid permeability, the cover does not appreciably prevent the flowing of a large flow of urine from the top of the wetting area V into the pocket 28. A non-broken inner cover layer also simplifies the manufacturing process for the diaper according to the invention.

In order to improve security against over-flow of urine from the wetting area V into the inner faeces receiving absorbent layer 14, the diaper has an extra barrier means 30 in the boundary region between the wetting area V and the faeces receiving area F. This barrier means 30 can, for example, have the shape of an erect front portion of the faeces receiving area of the inner cover layer 20, as is shown in FIG. 1. The barrier means 30 can have a hose-shaped fold 32 with an elastic element 34 placed therein to keep the barrier erect.

Figure 5:
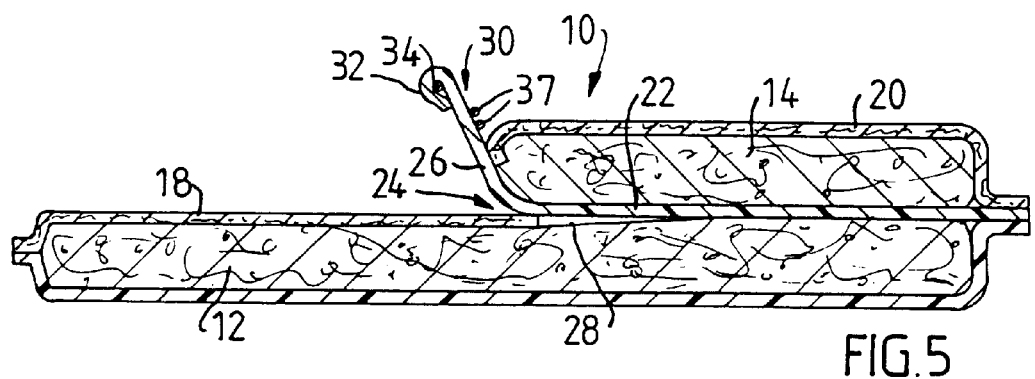
FIG. 5 shows a modification of the barrier means in the incontinence protector in longitudinal section.

Alternatively, the barrier means 30 can be formed as an extension of the front portion 26 of the liquid impermeable membrane 22, as is shown in FIGS. 4 and 5.

Other embodiments of the barrier means 30 are possible within the scope of the present invention. FIG. 3 shows how the barrier means 30 in a use position protrudes from the inside of the diaper 10 and forms a guide which can collect urine and guide it down through the opening 24 and the pocket 28, thus preventing urine from overflowing the front edge 26 of the essentially liquid impermeable membrane 22 and into the faeces receiving absorbent layer 14 of the diaper 10. The barrier means 30 also is designed to prevent transfer of faeces from the rear area F of the diaper 10 to the front wetting area V, so that faeces do not come into contact with the genitals of the user and the surrounding skin.

Furthermore, the diaper 10 according to the invention is designed to shape the opening 24 in a suitable manner, at least when the diaper is worn by the user. For this purpose, transverse elastic elements 36 can be arranged on the forward portion of the rear faeces receiving area of the inner cover layer 20. Alternatively, transverse elastic elements 37 can be applied on the membrane 22 in its front area. These transverse elastic elements 36 and 37 enable the outer elongated absorbent layer 12 to be curved laterally relative to the absorbent layer 14 and the membrane 22 lying inside of it thus forming the opening 24 and the pocket 28.

FIG. 6 shows an embodiment of the diaper 10 according to the invention, in which the rear both faeces and urine receiving portion of the diaper 10 is composed of a number of absorbent layers, in this case three layers 12, 14 and 38, where the essentially liquid impermeable membrane 22 is disposed between the layer 14 closest to the wearer and the intermediate layer 38, thus increasing the urine absorbent capacity in the rear portion of the diaper. The urine receiving pocket 28 can in this case be arranged between the layers 12 and 38 and/or alternatively between the layers 38 and the membrane 22.

Figure 7:
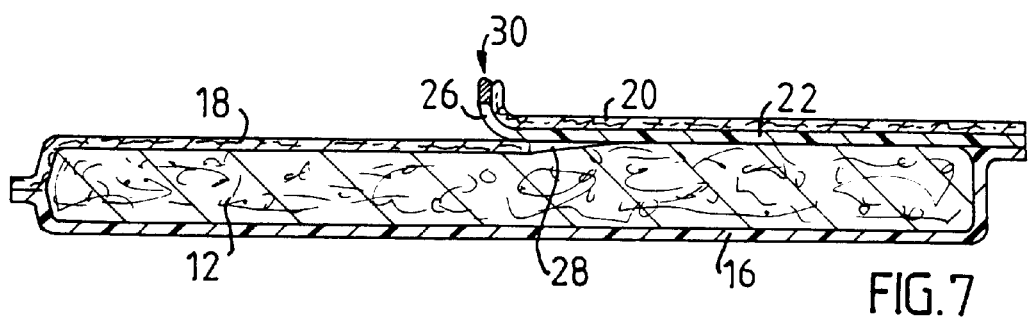
FIG. 7 shows an additional simplified embodiment of an incontinence protector according to the invention in longitudinal section.

FIG. 7 shows a simplified embodiment of the absorbent article according to the invention, where the inner absorbent layer 14 has been left out. In order to compensate for this to a certain extent, the inner cover layer 20 in the rear portion of the diaper 10 can be made of a material which is liquid absorbing in itself, and can be of relatively high bulk in order to be able to receive faeces containing relatively large proportions of liquid.

Figure 8:
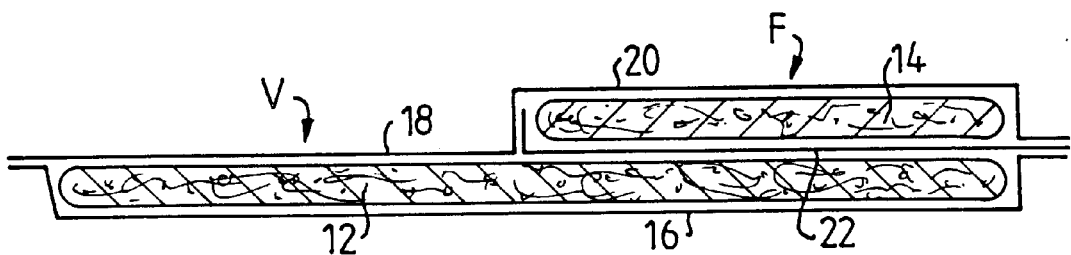
FIG. 8 shows schematically still another simplified embodiment of an absorbent article according to the invention.

A still more simplified embodiment of the diaper according to the invention is shown in FIG. 8, where the inner cover layer is unbroken and the barrier means at the front edge of the faeces receiving portion 7 has been eliminated.

Figure 9:
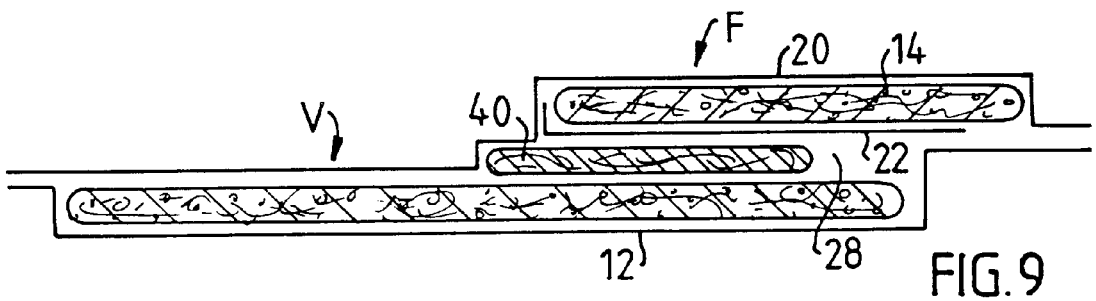
FIG. 9 shows an additional embodiment of the article according to the invention.

FIG. 9 shows a means for facilitating a rapid conducting of urine from the top of the wetting area V into the pocket 28 under the essentially liquid impermeable membrane 22, namely a layer 40 of a material with high liquid permeability, for example a batting material. This batting layer 40 can be placed between the membrane 22 and the elongated absorbent layer 12 and extend somewhat forward of the front edge portion of the absorbent layer 14 in the rear faeces receiving area F. The batting layer 40 can thus form a portion of the pocket 28 itself.

Figure 10:
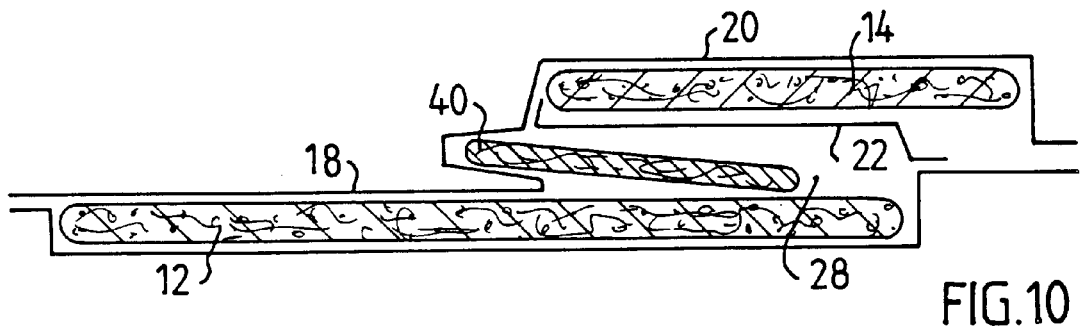
FIG. 10 shows a modification of the embodiment in FIG. 9.

In the embodiment in FIG. 10, the inner cover layer 18, 20 is folded in under the front portion of the batting layer 40, thus providing a more spacious and easily opened pocket 28. The elongated outer absorbent layer 12 does not need to extend over the entire rear portion of the diaper, as is shown in FIGS. 9 and 10. The liquid absorbent capacity of the diaper is dependent on the thickness of the rear portion of the diaper.

I claim:

1. An absorbent article comprising:
    an absorbent body with at least one elongated absorbent layer, which, on its inside facing the user is covered with a liquid permeable inner cover layer and which on its outside facing away from the user is covered by a liquid impermeable outer layer, said inner and outer cover layers being joined to each other along a peripheral edge of the absorbent body, said article having a rear, faeces receiving area and a front, urine absorbing wetting area,
    wherein an essentially liquid impermeable membrane is inlaid between the inner cover layer and the elongated absorbent layer only in the rear faeces receiving area of the article and is there joined to both cover layers along the edges of the elongated absorbent layer, said membrane preventing urine from being mixed with faeces in the rear area and there coming into contact with the skin of the wearer.

2. The absorbent article according to claim 1, wherein the inner cover layer, at least in the faeces receiving area of the article, has a liquid absorbing structure.

3. The absorbent article according the claim 1, wherein the absorbent body comprises, firstly, an outer absorbent layer, extending over essentially the entire length of the article, and secondly, at least one inner absorbent layer extending over the faeces receiving area of the article, between the essentially liquid impermeable membrane and the inner cover layer.

4. The absorbent article according to claim 1, wherein said membrane is joined to said cover layers along the edges coinciding with the peripheral edges of the elongated absorbent layer such that a transverse edge of said membrane forms an unjoined edge.

5. The absorbent article according to claim 4, wherein a pocket is disposed between the membrane and the elongated absorbent layer, at a position between the front and back areas of the article, to facilitate transport of urine from the front wetting area of the article to a rear area of the absorbent body, said unjoined transverse edge of the membrane providing an opening to said pocket.

6. The absorbent article according to claim 5, wherein the pocket comprises a layer of a material rapidly permeable to liquid, placed at least partially between the membrane and the elongated absorbent layer.

7. The absorbent article according to claim 6, wherein the inner cover layer is folded between the layer of material rapidly permeable to liquid and the elongated absorbent layer.

8. The absorbent article according to claim 6, wherein the material rapidly permeable to liquid is a batting material.

9. The absorbent article according to claim 5, wherein the inner cover layer has a transverse break to form an opening into the pocket between the membrane and the elongated absorbent layer.

10. The absorbent article according to claim 1, wherein the absorbent body comprises a plurality of inner absorbent layers located in the faeces receiving area of the article, at least the absorbent layer lying closest to the inner cover layer being insulated from underlying absorbent layers by means of the substantially liquid impermeable membrane.

11. The absorbent article according to claim 1, wherein the front area of the essentially liquid impermeable membrane is erected against a front portion of the rear faeces receiving area of the inner cover layer and is joined thereto.

12. The absorbent article according to claim 1, wherein the rear portion of the inner cover layer covering the wetting area is fixed to the essentially liquid impermeable membrane at least at the lateral edge portions of the article.

13. The absorbent article according to claim 1, wherein there projects from the inside of the article a barrier means, shaped to prevent urine from the wetting area from the flowing over to the rear faeces receiving area.

14. The absorbent article according to claim 13, wherein the barrier means is formed of a front portion of the faeces receiving area of the inner cover layer.

15. The absorbent article according to claim 13, wherein the barrier means is formed of a front portion of the essentially liquid impermeable membrane.

16. The absorbent article according to claim 13, wherein the barrier means has a hose-shaped fold in which there is disposed an elastic element.

17. The absorbent article according to claim 13, wherein the barrier means has well portions which extend entirely or partially around the wetting area of the article.

18. The absorbent article according to claim 1, wherein means are arranged to separate the membrane from the opposing portion of the elongated absorbent layer.

19. The absorbent article according to claim 18, wherein the separating means comprise transverse elastic elements arranged in the rear, faeces receiving area of the inner cover layer.

20. The absorbent article according to claim 18, wherein the separating means comprise transverse elastic elements arranged on the essentially liquid impermeable membrane.

* * * * *